United States Patent [19]

Strini et al.

[11] 3,968,179

[45] July 6, 1976

[54] SELECTIVE PREPARATION OF 1,2-DICHLOROETHANE

[75] Inventors: Jean-Claude Strini, St.-Auban; Jean-Raymond Costes, Dampierre, both of France

[73] Assignee: Rhone-Progil, Paris, France

[22] Filed: Dec. 21, 1973

[21] Appl. No.: 427,373

[30] Foreign Application Priority Data
Dec. 27, 1972 France ............................... 72.46390

[52] U.S. Cl. ................................................. 260/660
[51] Int. Cl.² ......................................... C07C 17/02
[58] Field of Search .................................... 260/660

[56] References Cited
UNITED STATES PATENTS

| | | | |
|---|---|---|---|
| 1,231,123 | 6/1917 | Brooks et al. | 260/660 |
| 2,393,367 | 1/1946 | Hammond | 260/660 |
| 2,765,353 | 10/1956 | Neher | 260/660 |
| 3,267,163 | 8/1966 | Tsutsumi et al. | 260/660 |
| 3,475,504 | 10/1969 | Kircher et al. | 260/660 |
| 3,839,475 | 10/1974 | Kurtz et al. | 260/660 |

FOREIGN PATENTS OR APPLICATIONS 960,083   6/1964   United Kingdom................ 260/660

*Primary Examiner*—Delbert E. Gantz
*Assistant Examiner*—Joseph A. Boska

[57] ABSTRACT

A process for the continuous chlorination of ethylene in the liquid phase in the absence of light and in the presence of 1,2-dichloroethane and dissolved ferric chloride wherein the reaction is carried out in a homogeneous reaction zone in which the reaction medium contains dissolved chlorine in an amount within the range of 1 to 20 g per kg of liquid reaction mixture and in which the ratio R between the molar hourly flow rate of ethylene introduced to the homogeneous reaction zone and the molar hourly flow rate of ethylene which saturates the 1,2-dichloroethane contained in the reaction zone is within the range of 0 to 140.

5 Claims, No Drawings

SELECTIVE PREPARATION OF 1,2-DICHLOROETHANE

The present invention relates to the preparation of 1,2-dichloroethane which is virtually free from 1,1,2-trichloroethane, and other higher chlorinated derivatives of ethane.

It is known that 1,2-dichloroethane can be produced by catalytic chlorination in liquid phase of ethylene at a temperature which is generally from 20° to 80° C., protected from moisture and light radiation. In most cases the liquid phase comprises 1,2-dichloroethane itself, and the catalyst which is most frequently used is ferric chloride since the apparatus in which chlorination of ethylene is carried out is generally made of ordinary steel, and the catalyst can thus be formed in situ.

During the course of chlorination of ethylene, chlorinated substitution derivatives of 1,2-dichloroethane are inevitably formed, the main one being 1,1,2-trichloroethane. The formation of such derivatives is revealed by drops in yield of 1,2-dichloroethane.

A certain number of solutions have been proposed for reducing such losses in yield. The use of a reaction temperature in the lower limit of the range of 20° to 80° C. can be mentioned in this respect. However, eliminating heat in this reaction, which is highly exothermic, at 20° C. or even at a temperature below 20° C., requires the use of an elaborate system for cooling the reaction medium, and this causes greater complexity in the manufacturing installation.

It has also been proposed that chlorination can be effected in two separate reaction vessels which are arranged in series, the first containing a more or less substantial amount of dissolved chlorine which is in excess with respect to the stoichiometry of the ratio for fixing one mole of chlorine on one mole of ethylene. However, this method does not permit the production of a 1,2-dichloroethane containing less than 1.1% by weight of chlorinated substitution derivatives of ethane which are more highly chlorinated than 1,2-dichloroethane, particularly 1,1,2-trichloroethane which is the main impurity.

Finally, it has been proposed that minor amounts of oxygen should be added to the chlorine in order to limit the reactions of substitution of 1,2-dichloroethane by chlorine.

However, in all the proposed solutions, the concentration of 1,1,2-trichloroethane is never less than 0.1% by weight and in most cases fluctuates around 0.5% by weight.

It is accordingly an object of the present invention to provide a process for the liquid phase chlorination of ethylene which overcomes the foregoing disadvantages, and it is a more specific object of the invention to provide a process for the preparation of 1,2-dichloroethane which contains less than 0.1 mole percent of 1,1,2-trichloroethane based upon the ethylene converted.

It has been found that one of the essential factors which influence the degree of selectivity of the reaction is the transfer of ethylene from the gaseous state which is the initial phase, to the state of being dissolved in liquid 1,2-dichloroethane, this being the phase in which the chlorination reaction occurs.

It was thus ascertained that the influence of this mass transfer on selectivity is directly linked to the value of the ratio R between the molar hourly flow rate of ethylene entering the homogeneous reaction zone, and the molar hourly flow rate of ethylene which saturates the 1,2-dichloroethane contained in that zone. The molar flow rate of ethylene which saturates the 1,2-dichloroethane in the homogeneous zone is defined as the product of the solubility of ethylene by the volume of liquid dichloroethane in the reaction zone, the amount of ethylene thus calculated being related to an hourly flow rate. The solubility of ethylene in liquid 1,2-dichloroethane is $3.10^{-2}$ mole/l at a temperature of 25° C., this value being taken as a reference value in determining the value of the ratio R.

In this way there is produced a 1,2-dichloroethane whose content of 1,1,2-trichloroethane, which is the main impurity, does not exceed 0.06% by weight.

The invention provides carrying out the reaction for the chlorination of ethylene, continuously, by means of molecular chlorine, at a temperature of from 20° to 80° C., protected from light radiation, in the presence of ferric chloride in a homogeneous reaction zone containing liquid 1,2-dichloroethane in which there is maintained an amount of dissolved chlorine which is from 1 to 20 g per kg of reaction mixture, and in which the ratio R as defined above is from 0 to 140.

In accordance with a preferred embodiment of the invention, the ratio R is in the range of from 50 to 90.

Nonetheless, values of the ratio R lower than 50, and even close to 0, are just as favorable as regards the degree of selectivity of the reaction. However, for a given production of 1,1,2-dichloroethane, such values require volumes of liquid which are considerable.

It is of advantage for chlorination to be carried out at a temperature of from 40° to 60° C. with a proportion of dissolved chlorine of from 2 to 10 g per kg of 1,2-dichloroethane, and an amount of ferric chloride of from 20 to 800 parts per million by weight of the reaction mixture and preferably from 60 to 200 parts per million. The ferric chloride can either be introduced into the homogeneous zone as such, or formed in situ by inter-reaction of the chlorine with the walls, made of steel or other iron alloys which are subject to attack by chlorine, with iron turnings or iron oxides introduced into said zone.

The molecular chlorine used according to the invention can either be in the form of liquid chlorine which is gasified before being reacted, or in the form of gaseous chlorine in the raw state, such as is collected at the outlet of chlorine manufacturing works. The yield in 1,2-dichloroethane is virtually unmodified whether liquid chlorine in a 99.9 percent state of purity or a chlorine in an 88–98 percent state of purity is used, the main impurities being $CO_2$, $O_2$, $N_2$, and $CO$. The chlorine used can be diluted by inert gases, that is to say, gases which do not react under the conditions of the reaction, for example, the gases just mentioned above. Dilution of chlorine by inert gases in a molar ratio which can reach 1/1 is not harmful to the reaction.

The molar proportion $Cl_2/C_2H_4$ used is from 0.9 to 1.1, but operation is preferably with a molar proportion of from 0.95 to 1.05.

According to the invention, the amount of moisture which can be present in the homogeneous zone is advantageously less than 80 parts per million by weight of the reaction mixture, in order to prevent the formation of secondary reactions, inter alia, an increasing formation of ethyl chloride.

Having described the basic concepts of the invention, reference is now made to the following examples which are provided by way of illustration, but not of limitation, of the practice of the invention.

EXAMPLE 1

A homogeneous zone is formed by a cylindrical steel reaction vessel, a circulating pump and a water cooler for removing the reaction heat. The pump which has an output varying from 200 to 800 liters/hour takes in the reaction mixture at the bottom of the reaction vessel and passes it through the cooler at the top of the reaction vessel. The whole of the homogeneous zone contains 3000 g of reaction mixture.

Chlorine and ethylene are introduced separately at the bottom of the reaction vessel. Mounted on top of the reaction vessel is a brine cooler for condensing 1,2-dichloroethane vapors. The discharges are passed to a series of two columns, a water column and a sodium hydroxide column, for removing hydrochloric acid and chlorine. The 1,2-dichloroethane produced overflows from the reaction vessel into a storage container.

Thus, 8.1 moles/h of 97 percent pure gaseous chlorine (impurities $N_2$, $O_2$, $CO$, $CO_2$, $H_2$) and 8.2 moles/h of ethylene are thus continuously introduced. The temperature of the reaction vessel is maintained at 45° C. The concentration of dissolved chlorine in the homogeneous zone is approximately 3g/kg of reaction medium. The ratio R between the molar hourly flow rate of ethylene entering the homogeneous reaction zone and the molar hourly flow rate of ethylene which saturates the 1,2-dichloroethane contained in said zone is approximately 110.

The amount of ferric chloride is 161 parts per million by weight and the moisture content in the reaction medium is 14 parts per million by weight.

After 18 hours of reaction, the 1,2-dichloroethane which is collected by overflowing contains 0.05% by weight of 1,1,2-trichloroethane.

By way of comparison, a test run for chlorinating $C_2H_4$ was carried out in the apparatus of Example 1 under the same operating conditions as that example, except that the ratio R as defined above is equal to 160, this being a value which is above the lower limit value of 140 according to the present application. After 18 hours, 0.25% by weight of 1,1,2-trichloroethane was formed. This amount is five times greater than that produced in Example 1.

EXAMPLE 2

5.05 moles/h of 97% pure chlorine and 5.05 moles/h of ethylene are continuously introduced into the apparatus of Example 1, the amount of dissolved chlorine in the homogeneous zone being approximately 3g/kg of reaction mixture. The temperature is maintained at 45° C. The amount of ferric chloride is 262 parts per million by weight of reaction mixture and the moisture content is 24 parts per million by weight.

The ratio R is 70. After 18 hours of reaction, the 1,2-dichloroethane produced contains only 0.035% by weight of 1,1,2-trichloroethane.

EXAMPLE 3

Operation is under conditions similar to those of Example 2, but 2.5 moles/h of 97% pure chlorine and 2.35 moles/h of ethylene are continuously introduced into the apparatus. The value of the ratio R as defined above is 35. After 24 hours of reaction, the 1,2-dichloroethane produced contains from 0.030 to 0.035% by weight of 1,1,2-trichloroethane.

The amount of ferric chloride is 310 parts per million by weight, and the moisture content is 48 parts per million by weight in the reaction mixture.

EXAMPLE 4

5.05 moles/h of 97% pure chlorine and 5.09 moles/h of ethylene are introduced continuously into the apparatus of Example 1. The amount of dissolved chlorine in the homogeneous zone is approximately 4g/kg of reaction mixture. The reaction temperature is fixed at 60° C. The reaction mixture contains 395 parts per million by weight of ferric chloride and 9 parts per million by weight of moisture. The ratio R as defined above reaches the value of 70. After 18 hours of the test run, the 1,2-dichloroethane produced contains 0.050% by weight of 1,1,2-trichloroethane.

The following comparative test uses a smaller amount of dissolved chlorine than the lower limit of the invention, 1 g/kg of liquid reaction medium.

5.05 moles/h of 97 percent pure chlorine and 5.1 moles/h of ethylene are continuously introduced into the apparatus as described in Example 1, the amount of dissolved chlorine in the homogeneous zone being approximately 0.6 g/kg of reaction mixture and the temperature being maintained at 60° C. The content of ferric chloride and moisture in the reaction medium is respectively 330 and 23 parts per million by weight. The ratio R is 70.

After 18 hours there is collected a 1,2-dichloroethane which contains 0.12% by weight of 1,1,2-trichloroethane, which corresponds to more than double the amount of 1,1,2-trichloroethane produced in Example 4.

EXAMPLE 5

5.05 moles/h of 97% pure chlorine and 4.9 moles/h of ethylene are introduced continuously into the apparatus of Example 1. The reaction temperature is maintained at 60° C. and the proportion of dissolved chlorine in the homogeneous zone is approximately 10 g/kg of reaction mixture. The proportion of ferric chloride is 485 parts per million by weight while the moisture content is 8 parts per million by weight. The ratio R is approximately 70. After 18 hours of reaction, the 1,2-dichloroethane produced contains 0.050 to 0.055% by weight of 1,1,2-trichloroethane.

It will be understood that various changes and modifications can be made in the details of formulation, procedure, and apparatus without departing from the spirit of the invention, especially as defined in the following claims.

We claim:

1. A process for the continuous liquid phase chlorination of ethylene with molecular chlorine at a temperature within the range of 20° to 80°C. in the absence of light and in the presence of liquid 1,2-dichloroethane containing ferric chloride dissolved therein to produce 1,2-dichloroethane along with less than 0.1 mole % of 1,1,2-trichloroethane based upon the ethylene converted comprising the steps of feeding to a reaction zone chlorine in an amount sufficient to provide dissolved chlorine within the range of 1 to 20 g per kg of liquid reaction mixture, maintaining the flow of ethylene to the reaction zone in an amount sufficient to provide a ratio R betwen the molar hourly flow rate of ethylene to the reaction zone and the molar hourly flow rate of ethylene which saturates the 1,2-dichloroethane contained in the reaction zone to within the range of close to 0 to 140, and recovering the 1,2-dichloroethane produced, with the ferric chloride being present in an amount within the range of 20–800 ppm by weight of the liquid reaction mixture and the molar ratio of $Cl_2/C_2H_4$ is within the range of 0.9 to 1.1.

2. A process according to claim 1 wherein the ratio R is in the range of from 50 to 90.

3. A process according to claim 1 wherein the molecular chlorine is a raw chlorine in a state of 88–98 percent purity.

4. A process according to claim 1 wherein the moisture content in the reaction zone is less than 80 parts per million by weight of the liquid reaction mixture.

5. A process for the continuous liquid phase chlorination of ethylene with molecular chlorine at a temperature within the range of 20° to 80°C in the absence of light and in the presence of 1,2-dichloroethane containing ferric chloride dissolved therein to produce 1,2-dichloroethane along with less than 0.1 mole % of 1,1,2-trichloroethane based upon the ethylene converted comprising the steps of feeding to a reaction zone chlorine in an amount sufficient to provide dissolved chlorine within the range of 1 to 20 g per kg of liquid reaction mixture, maintaining the flow of ethylene to the reaction zone in an amount sufficient to provide a ratio R between the molar hourly flow rate of ethylene to the reaction zone and the molar hourly flow rate of ethylene which saturates the 1,2-dichloroethane contained in the reaction zone less than 140 while maintaining the molar ratio of chlorine to ethylene within the range of 0.9 to 1.1, and recovering the 1,2-dichloroethane produced, with the ferric chloride being present in an amount within the range of 20–800 ppm based upon the weight of the liquid reaction mixture.

* * * * *